US009750847B2

United States Patent
Bee Eng Mary et al.

(10) Patent No.: US 9,750,847 B2
(45) Date of Patent: Sep. 5, 2017

(54) CHITOSAN HYDROGEL DERIVATIVES AS A COATING AGENT WITH BROAD SPECTRUM OF ANTIMICROBIAL ACTIVITIES

(71) Applicant: Nanyang Technological University, Singapore (SG)

(72) Inventors: Chan Bee Eng Mary, Singapore (SG); Poon Yin Fun, Singapore (SG); Mouad Lamrani, Lyon (FR); Shinichi Hamaguchi, Aichi (JP)

(73) Assignee: Nanyang Technological University, Singapore (SG)

( * ) Notice: Subject to any disclaimer, the term of this patent is extended or adjusted under 35 U.S.C. 154(b) by 0 days.

(21) Appl. No.: 14/922,369

(22) Filed: Oct. 26, 2015

(65) Prior Publication Data

US 2016/0038636 A1 Feb. 11, 2016

Related U.S. Application Data

(62) Division of application No. 14/209,602, filed on Mar. 13, 2014, now Pat. No. 9,199,000, which is a division
(Continued)

(51) Int. Cl.
*A61L 27/34* (2006.01)
*A61L 27/52* (2006.01)
(Continued)

(52) U.S. Cl.
CPC .............. *A61L 27/34* (2013.01); *A61K 8/042* (2013.01); *A61K 8/736* (2013.01); *A61L 27/20* (2013.01);
(Continued)

(58) Field of Classification Search
None
See application file for complete search history.

(56) References Cited

U.S. PATENT DOCUMENTS 8,709,470 B2   4/2014   Bee Eng Mary et al.
9,199,000 B2   12/2015  Bee Eng Mary et al.
(Continued)

FOREIGN PATENT DOCUMENTS

CN   1640913 A    7/2005
JP   H08-144121   6/1996
(Continued)

OTHER PUBLICATIONS

Poon et al., "Cytocompatible Hydrogels Based on Photocrosslinkable Methacrylated O-Carboxymethylchitosan with Tunable Charge: Synthesis and Characterization", Adv. Funct. Mater. 2007, 17, 2139-2150.*
(Continued)

*Primary Examiner* — Jianfeng Song
(74) *Attorney, Agent, or Firm* — Swanson & Bratschun, L.L.C.

(57) ABSTRACT

The present invention relates to water soluble quaternized chitosan derivatives which form hydrogel matrix with broad antimicrobial properties for the protection and coating of medical device. Hydrogel is attractive as an antimicrobial coating since its hydrophilicity intrinsically prevents the reversible nonspecific attachment of microbes. In order to achieve hydrogel formation, quaternized chitosan can be grafted with polymerizable groups, especially photocrosslinkable groups, such as methacrylates, PEG derivatives and be converted into hydrogels through a thermal or UV polymerization process. Hydrogels are hydrated cross-linked polymeric systems that contain water in an equilibrium state forming cushion water shield. The present invention is widely used in many medical devices. This invention
(Continued)

describes the formation of novel hydrogels based on quaternized ammonium chitosan derivatives which has been grafted with photocrosslinkable groups, hence providing hydrogels as antimicrobial water shield coating agent.

3 Claims, 4 Drawing Sheets

Related U.S. Application Data of application No. 13/383,684, filed as application No. PCT/JP2009/063013 on Jul. 13, 2009, now Pat. No. 8,709,470.

(51) Int. Cl.
| | |
|---|---|
| *A61L 31/04* | (2006.01) |
| *A61K 8/04* | (2006.01) |
| *A61K 31/14* | (2006.01) |
| *A61K 8/73* | (2006.01) |
| *A61Q 19/00* | (2006.01) |
| *A61L 27/54* | (2006.01) |
| *A61L 31/16* | (2006.01) |
| *A61L 27/20* | (2006.01) |
| *A61L 29/04* | (2006.01) |
| *A61L 29/08* | (2006.01) |
| *A61L 29/14* | (2006.01) |
| *A61L 31/10* | (2006.01) |
| *A61L 31/14* | (2006.01) |
| *C08B 37/08* | (2006.01) |
| *C08F 290/10* | (2006.01) |
| *C08G 81/00* | (2006.01) |
| *C08J 3/075* | (2006.01) |
| *C08J 3/24* | (2006.01) |
| *C08J 3/28* | (2006.01) |
| *G02B 1/04* | (2006.01) |

(52) U.S. Cl.
CPC .............. *A61L 27/52* (2013.01); *A61L 27/54* (2013.01); *A61L 29/043* (2013.01); *A61L 29/085* (2013.01); *A61L 29/145* (2013.01); *A61L 31/042* (2013.01); *A61L 31/10* (2013.01); *A61L 31/145* (2013.01); *A61L 31/16* (2013.01); *A61Q 19/00* (2013.01); *C08B 37/003* (2013.01); *C08F 290/10* (2013.01); *C08G 81/00* (2013.01); *C08J 3/075* (2013.01); *C08J 3/24* (2013.01); *C08J 3/28* (2013.01); *G02B 1/043* (2013.01); *A61L 2300/232* (2013.01); *A61L 2300/404* (2013.01); *C08J 2305/08* (2013.01)

(56) References Cited

U.S. PATENT DOCUMENTS

| | | |
|---|---|---|
| 2002/0031478 A1 | 3/2002 | Keller et al. |
| 2003/0125532 A1 | 7/2003 | Yoshii et al. |
| 2004/0258558 A1 | 12/2004 | Salamone et al. |
| 2005/0112182 A1 | 5/2005 | Minami et al. |
| 2014/0193476 A1 | 7/2014 | Bee Eng Mary et al. |

FOREIGN PATENT DOCUMENTS

| | | |
|---|---|---|
| JP | 2000-038403 | 2/2000 |
| JP | 2004-515813 | 5/2004 |
| JP | 2005-154477 | 6/2005 |
| JP | 2005-290297 | 10/2005 |
| JP | 2007-131731 | 5/2007 |

OTHER PUBLICATIONS

Dow (Product Safety Assessment, Kytamer® PC Humectant, [Downloaded May 14, 2012] [Retrieved from internet <URL: http://msdssearch.dow.com/PublishedLiteratureDOWCOM/dh__08a4/0901b803808a4cf0.pdf?fi lepath=productsafety/pdfs/no reg/233-00928.pdf&fromPage=GetDoc >]), 5 pages.

Extended European Search Report for EP 09847352, mailed Mar. 6, 2014, 5 pages.

Kim et al. (Apr. 1997) Polymer Bulletin 38:387-393 "Synthesis of Chitosan derivatives with quaternary ammonium salt and their antibacterial activity".

* cited by examiner

AFM (FC surface was observed. Left: 2×2×0.1μm, Right: 500×500×25nm)

Control (before Argon plasma treatment)

Argon plasma treated lens
Surface was activated and cleansed.

CS -coated lens
Chitosan hydrogel was grafted on the surface.

CHITOSAN HYDROGEL DERIVATIVES AS A COATING AGENT WITH BROAD SPECTRUM OF ANTIMICROBIAL ACTIVITIES

RELATED APPLICATIONS

This application is a divisional application of U.S. patent application Ser. No. 14/209,602, filed Mar. 13, 2014. U.S. patent application Ser. No. 14/209,602 is a divisional application of U.S. patent application Ser. No. 13/383,684 entitled "Chitosan Hydrogel Derivatives as a Coating Agent with Broad Spectrum of Antimicrobial Activities," filed Mar. 15, 2012, now U.S. Pat. No. 8,709,470. U.S. patent application Ser. No. 13/383,684 is a 35 USC §371 of PCT/JP2009/063013, filed Jul. 13, 2009. Each of these applications is hereby incorporated by reference in their entirety.

BACKGROUND ART

Chitosan is a β-1,4-linked polymer of glucosamine (2-amino-2-deoxy-β-D-glucose) and lesser amounts of N-acetylglucosamine. It is formed by the deacetylation of chitin (poly-N-acetylglucosamine), an abundant byproduct of the crab and shrimp processing industries.

The water solubility and antimicrobial property of native chitosan can be achieved or enhanced via the quaternization of chitosan. Quaternized chitosan, as a consequence of the quaternization of the amino group in the C-2 position, gained a permanent positive charge on the polysaccharide backbone. Quaternized chitosans find utility in cosmetic preparations, food preservation and packaging, coating materials, disinfectants and biomedical applications (JP-A-2005-290297, JP-A-8-144121, JP-A-2004-515813).

Hence, quaternized chitosan can be utilized for hydrogel formation and formulated as antimicrobial contact lens coating. In order to achieve hydrogel formation, quaternized chitosan can be grafted with photocrosslinkable groups, such as (meth)acrylates, and be converted into hydrogels through a UV polymerization process. Hydrogels are hydrated cross-linked polymeric systems that contain water in an equilibrium state and have been widely used in many biomedical applications including contact lenses, bio-implants such as urinary catheters, pacemaker, heart valves, artificial heart, mammary prosthesis, intraocular lenses, wound dressings, artificial organs and delivery carriers for the bioactive reagents due to their high degree of biocompatibility. However, there have been no studies on the use of quaternized chitosan hydrogels as antimicrobial medical device coating. The present invention describes the formation of novel hydrogels based on quaternized chitosan which has been grafted with polymerizable group, especially photocrosslinkable group, and relates to medical device having resultant antimicrobial activities.

SUMMARY OF THE INVENTION

The object of the present invention is to provide a novel and useful quaternized chitosan derivative, a method of producing the quaternized chitosan derivative, a chitosan hydrogel, a method of producing the hydrogel, and an article using the hydrogel.

The present invention provides following embodiments:
[1] A quaternized chitosan derivative having polymerizable organic moieties.
[2] The quaternized chitosan derivative of [1], having an ammonium group represented by the following formula (1):

$$-N^+(R^1)_3 \qquad (1)$$

where each $R^1$ is independently selected from the group consisting of hydrogen and a substituted or unsubstituted alkyl group, two or three of $(R^1)$s may combine to form a substituted or unsubstituted aliphatic cyclic group.
[3] The quaternized chitosan derivative of [2], wherein at least one of $(R^1)$s is a substituted or unsubstituted alkyl group having 1 to 18 carbon atoms.
[4] The quaternized chitosan derivative of any one of [1] to [3], wherein the polymerizable organic moiety is represented by the following formula:

$$-Y-P$$

(where P is a polymerizable group; Y is a spacer group).
[5] The quaternized chitosan derivative of [2], wherein said $-N^+(R^1)_3$ group is $-N^+R'R''_2$ where R' and R" are independently selected from the group consisting of hydrogen and a substituted or unsubstituted alkyl group, provided that R' has more carbon atoms than R".
[6] A method of producing a quaternized chitosan derivative having polymerizable organic moieties, comprising a step of reacting a quaternized chitosan derivative and a halide having a polymerizable organic moiety.
[7] The method of [6], wherein said halide is represented by the following formula (2):

$$X-P^1 \qquad (2)$$

where $P^1$ is a polymerizable organic moiety; X is a halogen atom. Preferred examples of X include Cl, Br and I. Preferred examples of the halide $X-P^1$ include $X-Z-COOCR^4=CH_2$ where $R^4$ is —H or —$CH_3$; Z is a chemical bond or a polyethylene glycol chain-containing group such as —$CH_2COO-(CH_2CH_2O)_n$— (n is 1 or more and preferably is 3 or more).
[8] A method of producing a chitosan hydrogel, comprising a step of polymerizing a polymerizable composition comprising said quaternized chitosan derivative of any one of [1] to [5], initiator, and water.
[9] A method of producing a chitosan hydrogel of [8], wherein said polymerizing step comprises a step of irradiating ultraviolet (UV) to a photopolymerizable composition comprising said quaternized chitosan derivative of any one of [1] to [5], photoinitiator, and water.
Preferred polymerizable (especially, photopolymerizable) composition comprises 0.1 to 20% by weight of said quaternized chitosan derivative of any one of [1] to [5], 0.1 to 1.0% by weight of initiator (especially, photoinitiator), 1 to 99.9% by weight of one or more comonomers, and 0 to 80% by weight of water per the total amount of the composition. The composition may contain other components, provided that the advantage of the present invention is not impaired.
[10] A hydrogel produced by the method of [8] or [9].
[11] A medical device having a coating comprising the hydrogel of [10].
[12] A contact lens having a coating comprising the hydrogel of [10].

[13] A medical device containing the hydrogel of [10].
[14] A cosmetic containing the hydrogel of [10].

BRIEF DESCRIPTION OF THE DRAWINGS

FIG. 1(a) corresponds to unquaternized chitosan hydrogel; FIG. 1(b) corresponds to trimethylammonium chitosan-g-PEGMA hydrogel; FIG. 1(c) corresponds to trihexylammonium chitosan-g-PEGMA hydrogel; FIG. 1(d) corresponds to tridecylammonium chitosan-g-PEGMA hydrogel; FIG. 1(e) corresponds to dimethylhexylammonium chitosan-g-PEGMA hydrogel; and FIG. 1(f) corresponds to dimethyldecylammonium chitosan-g-PEGMA.

DESCRIPTION OF EMBODIMENTS

Figure 1:
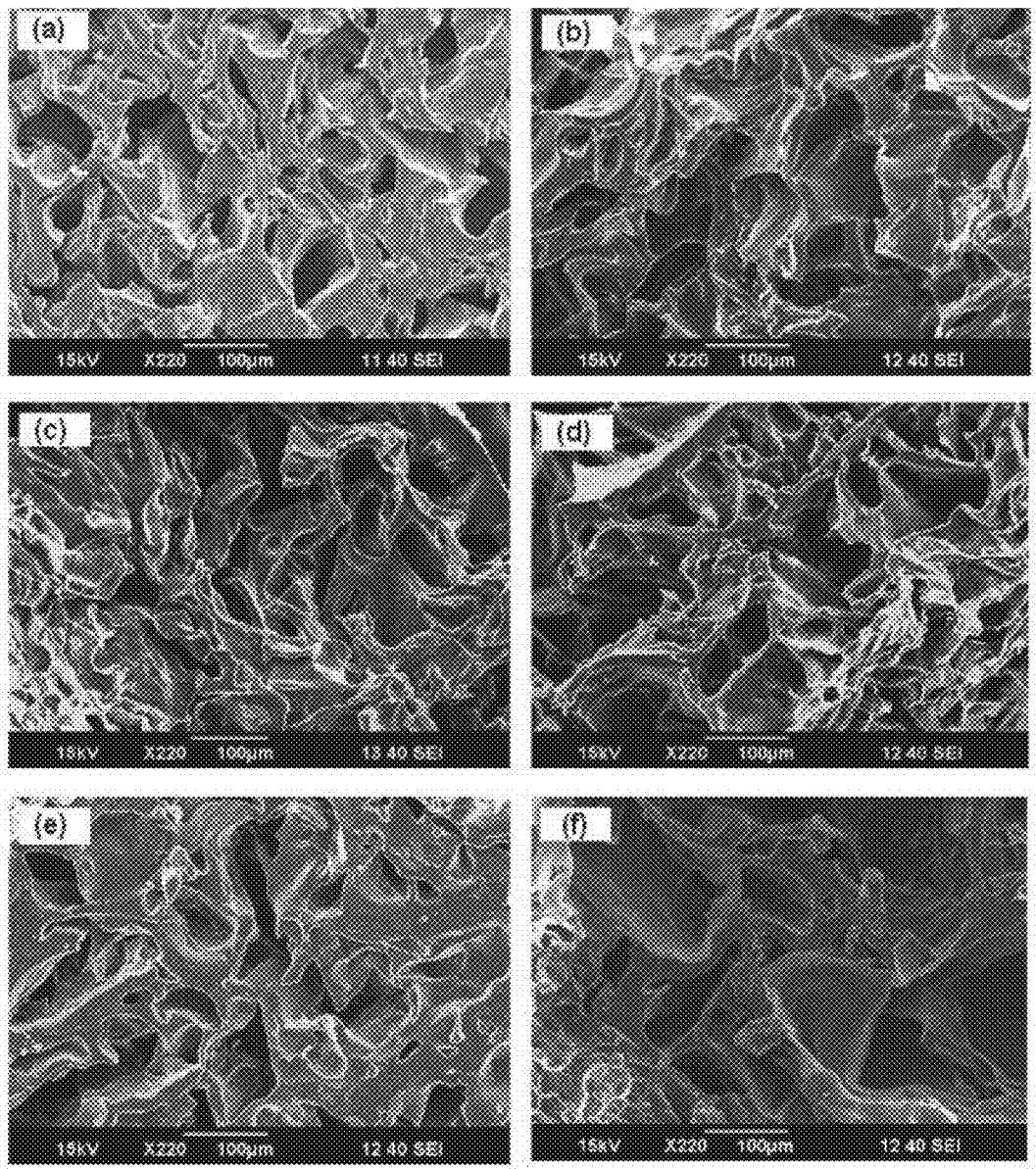
FIG. 1 shows scanning electron micrographs of several chitosan based hydrogels (Example 15).

The present invention relates to water soluble quaternized chitosan derivatives which form hydrogel matrix with broad antimicrobial properties for the protection and coating of medical device. Hydrogel is attractive as an antimicrobial coating since its hydrophilicity intrinsically prevents the reversible nonspecific attachment of microbes.

In order to achieve hydrogel formation, quaternized chitosan can be grafted with polymerizable groups, especially photocrosslinkable groups, such as methacrylates, PEG derivatives and be converted into hydrogels through a thermal or UV polymerization process. Hydrogels are hydrated cross-linked polymeric systems that contain water in an equilibrium state forming cushion water shield. The present invention is widely used in many medical devices for example biomedical devices such as contact lenses, bio-implants such as urinary catheters, pacemaker, heart valves, artificial heart, mammary prosthesis, intraocular lenses, wound dressings, artificial organs and delivery carriers for the bioactive reagents, total joint replacement due to their high degree of biocompatibility, antimicrobial property and good wetting characteristics. This invention describes the formation of novel hydrogels based on quaternized ammonium chitosan derivatives which has been grafted with polymerizable groups, especially photocrosslinkable groups, hence providing hydrogels as antimicrobial water shield coating agent.

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

In a first, highly preferred embodiment, the inventive antimicrobial hydrogels comprise a crosslinked hydrogel prepared by the free radical polymerization of a polymerizable cationic quaternized chitosan.

A schematical structure of the polymerizable cationic quaternized chitosan is shown in following formula (3):

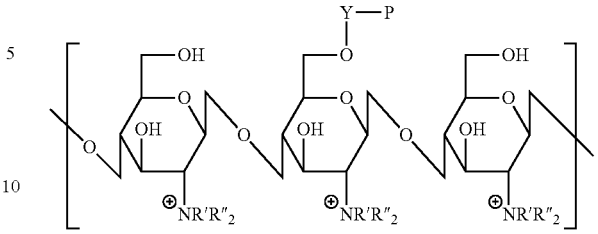

(3)

where P is a polymerizable group; Y is a spacer group; and R' and R" are independently selected from the group consisting of hydrogen and a substituted or unsubstituted alkyl group. Formula (3) is illustrated for only explanation of the present invention. It should be noted that the polymerizable quaternized chitosan of the present invention is not limited to an embodiment of formula (3).

The cationic quaternized chitosan is preferably prepared from a quaternised chitosan derivative, although other cationic quaternized chitosans may be used. These cationic quaternized chitosans contain trialkylammonium groups along the quaternized chitosan chain. The quaternized chitosan will also contain a polymerizable group attached to the quaternized chitosan chain via a primary hydroxyl group, preferably via a spacer group Y.

Referring to formula (3), preferred embodiments of the cationic quaternized chitosan will comprise a quaternized chitosan containing trialkylammonium groups along the polymer chain, wherein all three alkyl groups are identical. Non-limiting Examples of the quaternized ammonium moiety include trimethylammonium-, triethylammonium-, tripropylammonium-, tributylammonium-, tripentylammonium-, trihexylammonium-, trioctylammonium-, tridecylammonium-, tridodecylammonium-, trioctadecylammonium-.

More preferred are trialkylammonium moieties wherein one alkyl group differs from the other two. Non-limiting Examples of this more preferred embodiment include dimethylethylammonium-, dimethylpropylammonium-, dimethylbutylammonium-, dimethylpentylammonium-, dimethylhexylammonium-, dimethyloctylammonium-, dimethyldecylammonium-, dimethyldodecylammonium-, dimethyloctadecylammomium-dihexadecylmethylammonium-, dihexadecylethylammonium-, dihexadecylpropylammonium-, and dihexadecylbutylammonium-.

Again, referring to formula (3), the polymerizable group P may comprise one of the polymerizable groups selected from the group comprising vinyl, acrylate, methacrylate, vinyl phenylene, cinnamoyl, allyl. The polymerizable group P is preferably attached to the cationic quaternized chitosan via a spacer group Y. The spacer group may be selected from the group comprising —$(C_nH_{2n})$—, or more preferably —$(C_nH_{2n}O)$—, wherein n=0 to 20, or more preferably between 2 and 10.

In a preferred embodiment, the hydrogel is produced by the free radical polymerization of the polymerizable cationic quaternized chitosan. In another preferred embodiment, the polymerizable cationic quaternized chitosan may be copolymerized with a comonomer selected from the non-limiting group comprising acrylic acid, methyl acrylate, ethyl acrylate, hydroxyethyl acrylate, hydroxypropyl acrylate, glycerol monoacrylate, acryloylphosphorylcholine, polyethylene glycol diacrylate, methacrylic acid, methyl methacrylate, ethyl methacrylate, hydroxyethyl methacrylate, hydroxypropyl methacrylate, glycerol monomethacrylate, methacryloylphosphorylcholine, polyethylene glycol di(meth)acrylate, styrene and N-vinyl pyrrolidinone, or mixtures thereof. The examples of the comonomer also include difunctional or trifunctional monomers such as ethylene glycol diacrylate, glycerol diacrylate, glycerol triacrylate, divinylbenzene, polyethylene glycol diacrylate, ethylene glycol di(meth)acrylate, glycerol di(meth)acrylate, glycerol tri(meth)acrylate, divinylbenzene, polyethylene glycol di(meth)acrylate, glycidyl acrylate, glycidyl(meth)acrylate, polypropylene glycol di(meth)acrylate, polyoxyethylene-polyoxypropylene blockcopolymer and mixtures thereof.

Heretofore, trialkylammonium chitosan can be synthesized through reacting with alkyl halide such as methyl iodide, hexyl bromide or decyl bromide in a nucleophilic substitution reaction with the resultant formation of the quaternized structure. See following reaction scheme I. In the present invention, preferred starting materials include chitosan powder with a degree of deacetylation of preferably at least 70%, more preferably at least 75%, and preferably number average molecular weight of 10,000 to 200,000 g/mol (determined through GPC). When the molecular weight of the starting chitosan material is excessively high, it is difficult to polymerize the chitosan derivative of the present invention. In this event, fixation of a hydrogel to a surface of a substrate would also be difficult.

Scheme I: The reaction scheme used in the preparation of trialkylammonium macromonomers and hydrogels therefrom.

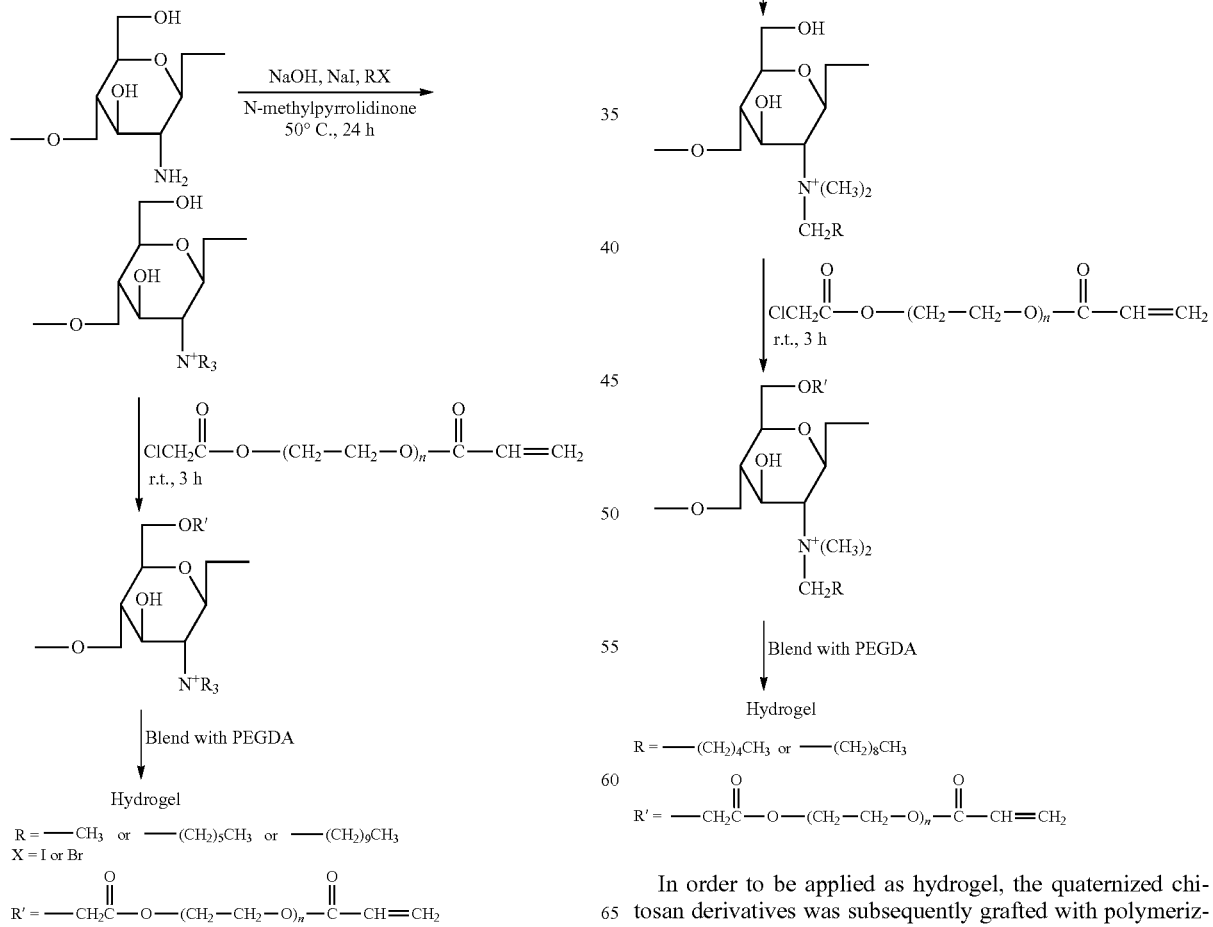

N-alkyl-N,N-dialkylammonium chitosan can also be formed by first reductively alkylating chitosan with aldehydes (such as hexanal and decanal) to form imines, followed by reduction to obtain N-alkyl derivatives. The alkyl derivative was then quaternized with alkyl halide such as methyl iodide. See following reaction scheme II.

Scheme II: The reaction scheme used in the preparation of dimethylalkylammonium macromonomers and hydrogels therefrom.

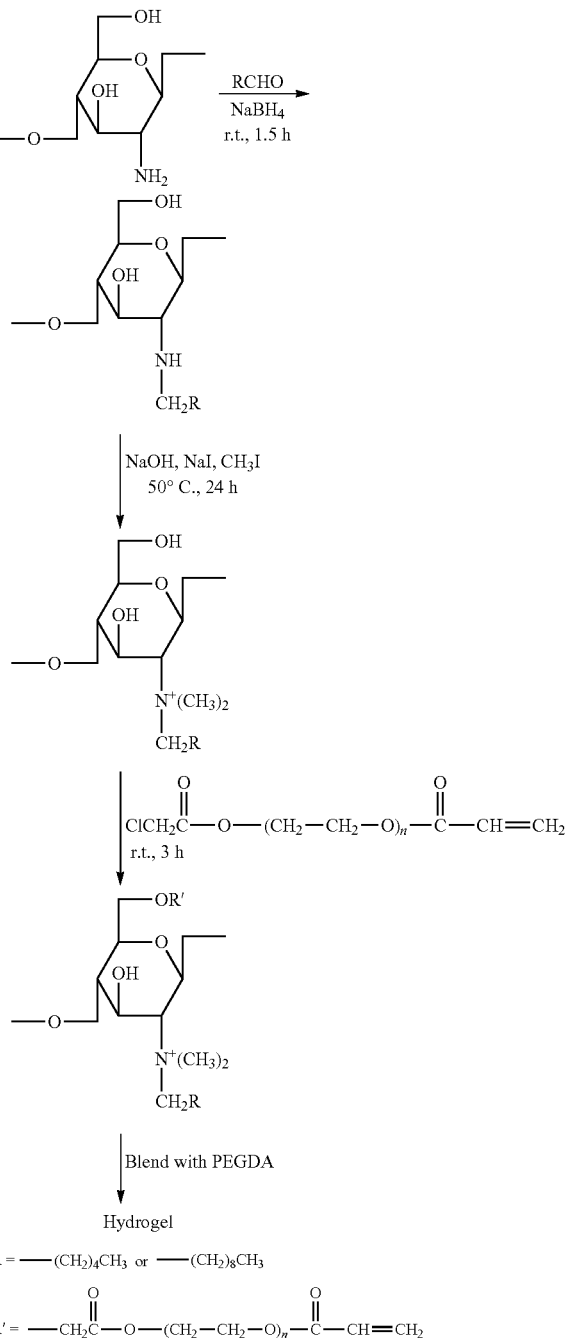

In order to be applied as hydrogel, the quaternized chitosan derivatives was subsequently grafted with polymerizable groups, especially photocrosslinkable groups and converted to hydrogels via a thermal or UV polymerization process. The photocrosslinkable group used here is polyethylene glycol monoacrylate (PEGMA). Chitosan and the quaternized chitosan were each grafted with PEGMA (of a low molecular weight of 375), leading to the formation of chitosan-g-PEGMA and quaternized chitosan-g-PEGMA. Chitosan-g-PEGMA and quaternized chitosan-g-PEGMA were respectively synthesized through reacting chlorofunctionalised PEGMA with native chitosan or quaternized chitosan, using sodium hydroxide as base. After grafting reaction, the water solubility of the quaternized chitosans were not changed while chitosan, after grafting with the hydrophilic PEGMA, changed from insoluble to soluble. The presence of grafted PEG can be detected by using UV spectroscopy employing a PEG assay.

Polyethylene glycol diacrylate (PEGDA), polyethylene glycol dimethacrylate, polypropylene glycol di(meth)acrylate, or polyoxyethylene-polyoxypropylene blockcopolymer can be blended with the photocrosslinkable, quaternized chitosan derivatives during UV irradiation. PEGDA has been widely used in photochemical modification for the use of hydrogel scaffold, membrane material and drug delivery. Blending with the photocrosslinkable PEGDA has several advantages due to its hydrophilicity, biocompatibility and biodegradability. In addition, PEG being an uncharged polymer, has minimal interaction with itself and other molecules. The most important reason is that by blending with PEGDA, the tensile strength of the chitosan derivatives, in the current invention, can be improved, resulting in hydrogels which can be easily handled.

In this invention, photopolymerisation was used to produce hydrogels due to its many advantages. Photopolymerisation is a versatile and facile technique to produce water-insoluble hydrogels from liquids. It is also a non-invasive technique where hydrogels can be formed in a short time under ambient temperature without any detrimental effects to the hydrogels' components. Low organic solvent level was also involved in the process and the use of toxic chemical crosslinkers (in conventional chemical crosslinking) such as epichlorohydrin, glutaraldehyde, carbodiimide and so on are avoided. UV light was used to interact with light sensitive compounds called photoinitiators to create free radicals that can initiate polymerization to formed crosslinked hydrogels. Hence, hydrogels can be made from solutions consisting of chitosan-g-PEG acrylate or quaternized chitosan-g-PEG acrylate and PEG diacrylate in 2:1 ratio (20 wt % total polymer mixture and 80 wt % water) with small amount of water-soluble photoinitiator (Irgacure 2959) (0.1 wt % with respect to the polymer mixture). This will form the full interpenetrating network system where the chitosan derivatives were copolymerized with the PEGDA. After dissolution, around 0.25 ml of each solution was added to polypropylene tube and placed in a glass chamber with argon purge. The sample solution in glass chamber was exposed to UV for 15 min for hydrogel formation. Alternatively, photopolymerisation can also be carried out on glass slides with a spacer frame of 250 μm thick. The precursor solution was dropped onto the glass slide, covered with another glass slide and then exposed to UV for 15 min, thus producing the hydrogel.

Larger pore size of freeze-dried polymers can be achieved via N-alkylation of chitosan. The SEM cross-sectional images for the freeze-dried polymers of the chitosan and some quaternized chitosan are shown in FIG. 1. FIG. 1 shows that the unquaternized chitosan hydrogel has many small pores (of a few micrometers) and the quaternized chitosan hydrogels generally have larger pores greater than 100 μm under the same magnification (×220). Dimethyldecylammonium chitosan hydrogel (see Synthetic Example 14) was observed to have relatively larger pores compared to dimethylhexylammonium chitosan hydrogel (see Synthetic Example 13). Other applications:

The antimicrobial hydrogels described herein exhibit potent antimicrobial activity against bacteria and fungi, thus they can be used not only as contact lens coating, but also be included in formulations where it is desirable to minimize bacterial attack. For example, they may be incorporated at low concentrations into cosmetic formulations, such as hair and skin formulations or into contact lens solutions.

These chitosan derivative hydrogels may also applied as biomedical or pharmaceutical materials which can be applied onto or contacted with the body surface of humans or other animals in order to prevent or inhibit the proliferation of microorganisms therein.

The antimicrobial hydrogels, prepared from biocompatible materials such as PEG and chitosan, can also be used in the field of tissue engineering, engaging in 2-dimensional or 3-dimensional cell culture. The antimicrobial hydrogels, due to the presence of positive charge, can also be used in the delivery and controlled release of negatively charged bioactive materials such as growth factors or cell adhesive proteins.

SYNTHETIC EXAMPLES

Chitosan powder was supplied by Dalian Xindie Chitin Co., China with a degree of deacetylation of 81.79% and number average molecular weight of $1.05 \times 10^5$ g/mol (determined through GPC). N-methyl-2-pyrrolidinone, sodium iodide, methyl iodide, hexyl bromide, decyl bromide, hexanal, decanal, chloroacetyl chloride, PEG monoacrylate ($M_n$ 375), PEG diacrylate ($M_n$ 700), potassium carbonate, sodium hydroxide, isopropanol and sodium borohydride were purchased from Sigma-Aldrich (Saint Louis, Mo., USA). Analytical grade hexane, toluene, diethyl ether, ethanol, acetone and methylene chloride were purchased from VWR Pte Ltd (Singapore) and used as received. Toluene was dried over molecular sieves. The photoinitiator, 4-(2-hydroxyethoxy)phenyl-(2-hydroxy-2-propyl) ketone (Irgacure 2959) was purchased from Ciba (Singapore).

$^1$H-NMR and $^{13}$C-NMR spectra were recorded with a Bruker Avance 300 MHz instrument. Fourier Transform Infra Red (FTIR) spectra were recorded at room temperature using a Digilab FTS 3100 instrument over the wavenumber range of 4000-400 $cm^{-1}$ using KBr disks. For Scanning Electron Microscopy (SEM), the hydrogels were immersed in deionised water for 2 days or longer prior observation. These hydrogels were then frozen at −50° C. in the freeze dryer for three hours before they were vacuum dried. After 48 h of freeze-drying, the hydrogels were cut with a sharp scalpel to obtain the cross-section. They were then mounted onto an aluminium stud and sputter-coated with platinum for 60 s using a Jeol JFC-1600 Auto Fine coater. The samples were then imaged by scanning electron microscope (Jeol JSM-5600LV).

Synthetic Example 1: Preparation of Chlorofunctionalised PEG Acrylate

PEG monoacrylate (2.36 ml, 7.06 mmol), with a number average molecular weight of 375, was dissolved in 100 ml toluene and treated with chloroacetylchloride (2.25 ml, 28.24 mmol). The mixture was then heated under reflux for 24 hours. After this time, the solvent and volatiles were removed by evaporation and the residue was dissolved in methylene chloride (150 ml). The solution was stirred over potassium carbonate and filtered. The solvent was removed through evaporation and after washing with hexane, the product was obtained and dried, and used without further purification.

$^1$H-NMR (300 MHz, CDCl$_3$), δ: 3.5-3.7 (—O—C$\underline{H}_2$—C$\underline{H}_2$—O—), 4.1 (Cl—C$\underline{H}_2$—COO—), 5.7 (—C$\underline{H}$=CH$_2$), 6.0, 6.2 (—CH=C$\underline{H}_2$)

$^{13}$C-NMR (300 MHz, CDCl$_3$), δ: 63.6-69.0 (—O—$\underline{C}$H$_2$—$\underline{C}$H$_2$—O—), 128, 131 (—$\underline{C}$H=$\underline{C}$H$_2$), 166 (—O$\underline{C}$O—CH=CH$_2$), 167 (Cl—CH$_2$—$\underline{C}$OO—)

Synthetic Example 2: Preparation of Trimethylammonium Chitosan

Chitosan (1 g) was added to N-methyl-2-pyrrolidinone (50 ml) and treated with 1.5 N NaOH solution (15 ml). The mixture was stirred for 30 min at 50° C. Sodium iodide (1.08 g) and methyl iodide (11.2 g) were then added to the solution, which was then stirred for 24 hours at 50° C. The reaction mixture was then filtered to remove the insoluble material, and the filtrate was then precipitated into a large excess of acetone and filtered. The resulting product collected by filtration, and dried under vacuum.

$^1$H-NMR (300 MHz, D$_2$O), δ: 1.95 (—NHCOC$\underline{H}_3$) 3.33 (—N$^+$C$\underline{H}_3$), 3.4-4.1 (chitosan-$\underline{H}$-2-6)

Synthetic Example 3: Preparation of Trihexylammonium Chitosan

Trihexylammonium chitosan was prepared in the same manner as Synthetic Example 2 except for changing from methyl iodide (11.2 g) to hexyl bromide (13.0 g).

$^1$H-NMR (300 MHz, D$_2$O), δ: 0.74 (—N$^+$CH$_2$CH$_2$(CH$_2$)$_3$C$\underline{H}_3$), 1.19 (—N$^+$CH$_2$CH$_2$(C$\underline{H}_2$)$_3$CH$_3$), 1.25 (—N$^+$CH$_2$C$\underline{H}_2$(CH$_2$)$_3$CH$_3$), 1.95 (—NHCOC$\underline{H}_3$) 3.07 (—N$^+$C$\underline{H}_2$CH$_2$(CH$_2$)$_3$CH$_3$), 3.4-4.1 (chitosan-$\underline{H}$-2-6)

Synthetic Example 4: Preparation of Tridecylammonium Chitosan

Tridecylammonium chitosan was prepared in the same manner as Synthetic Example 2 except for changing from methyl iodide (11.2 g) to decyl bromide (17.4 g).

$^1$H-NMR (300 MHz, D$_2$O), δ: 0.74 (—N$^+$CH$_2$CH$_2$(CH$_2$)$_7$C$\underline{H}_3$), 1.16 (—N$^+$CH$_2$CH$_2$(C$\underline{H}_2$)$_7$CH$_3$), 1.58 (—N$^+$CH$_2$ C$\underline{H}_2$ (CH$_2$)$_7$CH$_3$), 1.94 (—NHCOC$\underline{H}_3$), 3.02 (—N$^+$C$\underline{H}_2$CH$_2$(CH$_2$)$_7$CH$_3$), 3.4-4.1 (chitosan-$\underline{H}$-2-6)

Synthetic Example 5: Preparation of Chitosan-g-PEGMA

Chitosan (0.2 g) was added to a solution of 50 wt % NaOH solution (2.5 ml), and stirred for 24 h. The alkalized chitosan was then filtered, and the filtrate transferred into a flask. Chlorofunctionalised PEG acrylate (0.5 g, see Synthetic Example 1) was dissolved in isopropanol (2.5 ml) and added dropwise into the chitosan with stirring. The mixture was reacted for 24 h at room temperature. After this time, the crude product was recovered by filtration, and dissolved in water (10 ml). The solution was neutralised with 2.5M HCl. After centrifugation of the solution to remove the precipitate and addition of ethanol (40 ml) to the supernatant, the product precipitated from the solution. The solid was filtered and rinsed thrice with ethanol.

$^1$H-NMR (300 MHz, D$_2$O), δ: 1.94 (—NHCOC$\underline{H}_3$), 3.5-3.7 (—O—C$\underline{H}_2$—C$\underline{H}_2$—O—), 3.4-4.1 (chitosan-$\underline{H}$-2-6), 5.5 (—C$\underline{H}$=CH$_2$), 6.02 (—CH=C$\underline{H}_2$)

Synthetic Example 6: Preparation of Trimethylammonium Chitosan-g-PEGMA

Trimethylammonium chitosan (0.2 g, see Synthetic Example 2) in 0.45 ml water was added with 0.30 ml of 0.38 M sodium hydroxide solution. Chlorofunctionalised PEG acrylate (0.5 g, see Synthetic Example 1) dissolved in 1.5 ml isopropanol was then added with stirring and the mixture stirred at room temperature for 3 h. After the reaction, the mixture was cooled to room temperature and precipitated in a mixture of acetone and ethanol. The product was obtained after filtration.

$^1$H-NMR (300 MHz, D$_2$O), δ: 1.95 (—NHCOC$\underline{H}_3$), 3.22 (—N$^+$C$\underline{H}_3$), 3.5-3.7 (—O—C$\underline{H}_2$—C$\underline{H}_2$—O—), 3.4-4.1 (chitosan-$\underline{H}$-2-6), 5.5 (—C$\underline{H}$=CH$_2$), 5.9-6.1 (—CH=C$\underline{H}_2$)

Synthetic Example 7: Preparation of Trihexylammonium Chitosan-g-PEGMA

Trihexylammonium chitosan-g-PEGMA was prepared in the same manner as Synthetic Example 6 except for changing from trimethylammonium chitosan (0.2 g) to trihexylammonium chitosan (0.2 g, see Synthetic Example 3).

$^1$H-NMR (300 MHz, D$_2$O), δ: 0.86 (—N$^+$CH$_2$CH$_2$(CH$_2$)$_3$C$\underline{H}_3$), 1.19 (—N$^+$CH$_2$CH$_2$(C$\underline{H}_2$)$_3$CH$_3$), 1.30 (—N$^+$CH$_2$ C$\underline{H}_2$(CH$_2$)$_3$CH$_3$), 1.95 (—NHCOC$\underline{H}_3$), 3.07 (—N$^+$C$\underline{H}_2$CH$_2$(CH$_2$)$_3$CH$_3$), 3.5-3.7 (—O—C$\underline{H}_2$—C$\underline{H}_2$—O—), 3.4-4.1 (chitosan-$\underline{H}$-2-6), 5.6 (—C$\underline{H}$=CH$_2$), 5.97-6.2 (—CH=C$\underline{H}_2$)

Synthetic Example 8: Preparation of Tridecylammonium Chitosan-g-PEGMA

Tridecylammonium chitosan-g-PEGMA was prepared in the same manner as Synthetic Example 6 except for changing from trimethylammonium chitosan (0.2 g) to tridecylammonium chitosan (0.2 g, see Synthetic Example 4).

$^1$H-NMR (300 MHz, D$_2$O), δ: 0.74 (—N$^+$CH$_2$CH$_2$(CH$_2$)$_7$C$\underline{H}_3$), 1.16 (—N$^+$CH$_2$CH$_2$(C$\underline{H}_2$)$_7$CH$_3$), 1.58 (—N$^+$CH$_2$ C$\underline{H}_2$(CH$_2$)$_7$CH$_3$), 1.94 (—NHCOC$\underline{H}_3$), 3.02 (—N$^+$C$\underline{H}_2$CH$_2$(CH$_2$)$_7$CH$_3$), 3.5-3.7 (—O—C$\underline{H}_2$—C$\underline{H}_2$—O—), 3.4-4.1 (chitosan-$\underline{H}$-2-6), 5.6 (—C$\underline{H}$=CH$_2$), 5.91-6.05 (—CH=C$\underline{H}_2$)

Synthetic Example 9: Preparation of N-Hexyl Chitosan

Chitosan (1.0 g, 6.21 mmol) was dissolved in 1% aq. acetic acid (100 ml). Hexanal (0.62 g, 0.74 ml, 1 eqv.) was then added, and the mixture stirred at room temperature. After 1 hour of stirring, the pH of the solution was adjusted to 4.5. To this solution, 10% aq. solution of sodium borohydride (9.32 mmol) was added and the solution stirred for an additional 90 minutes. After this time, the pH of the solution was adjusted to 10, and the precipitated N-hexyl chitosan collected by filtration, and washed with water until the filtrate was of neutral pH. These precipitants were filtered and the residue washed with distilled water to neutrality. The unreacted aldehyde and inorganic products were soxhlet extracted with ethanol and diethyl ether. The resulting N-hexyl chitosan was filtered and dried.

Synthetic Example 10: Preparation of N-Decyl Chitosan

N-decyl chitosan was prepared in the same manner as Synthetic Example 9 except for changing from hexanal (0.62 g) to decanal (0.97 g, 6.2 mmol).

Synthetic Example 11: Preparation of Dimethylhexylammonium Chitosan

N-Hexyl chitosan (1 g, see Synthetic Example 9) was added to N-methyl-2-pyrrolidinone (50 ml) and treated with 1.5 N NaOH solution (15 ml). The mixture was stirred for 30 min at 50° C. Sodium iodide (1.08 g) and methyl iodide (11.2 g) were then added to the solution, which was then stirred for 24 hours at 50° C. The reaction mixture was then filtered to remove the insoluble material, and the filtrate was then precipitated into a large excess of acetone and filtered. The resulting product was collected by filtration, and dried under vacuum.

$^1$H-NMR (300 MHz, D$_2$O), δ: 0.76 (—N$^+$CH$_2$CH$_2$(CH$_2$)$_3$C$\underline{H}_3$), 1.22 (—N$^+$CH$_2$CH$_2$(C$\underline{H}_2$)$_3$CH$_3$), 1.58 (—N$^+$CH$_2$C$\underline{H}_2$(CH$_2$)$_3$CH$_3$), 1.96 (—NHCOC$\underline{H}_3$), 3.24 (—N$^+$C$\underline{H}_3$), 3.4-4.1 (chitosan-$\underline{H}$-2-6)

Synthetic Example 12: Preparation of Dimethyldecylammonium Chitosan

Dimethyldecylammonium chitosan was prepared in the same manner as Synthetic Example 11 except for changing from N-hexyl chitosan (1 g) to N-decyl chitosan (1 g, see Synthetic Example 10). $^1$H-NMR (300 MHz, D$_2$O), δ: 0.71 (—N$^+$CH$_2$CH$_2$(CH$_2$)$_7$C$\underline{H}_3$), 1.17 (—N$^+$CH$_2$CH$_2$(C$\underline{H}_2$)$_7$CH$_3$), 1.58 (—N$^+$CH$_2$ C$\underline{H}_2$(CH$_2$)$_7$CH$_3$), 1.94 (—NHCOC$\underline{H}_3$), 3.23 (—N$^+$C$\underline{H}_3$), 3.4-4.1 (chitosan-$\underline{H}$-2-6)

Synthetic Example 13: Preparation of Dimethylhexylammonium Chitosan-g-PEGMA

Dimethylhexylammonium chitosan-g-PEGMA was prepared in the same manner as Synthetic Example 6 except for changing from trimethylammonium chitosan (0.2 g) to dimethylhexylammonium chitosan (0.2 g, see Synthetic Example 11).

$^1$H-NMR (300 MHz, D$_2$O), δ: 0.75 (—N$^+$CH$_2$CH$_2$(CH$_2$)$_3$C$\underline{H}_3$), 1.22 (—N$^+$CH$_2$CH$_2$(C$\underline{H}_2$)$_3$CH$_3$), 1.58 (—N$^+$CH$_2$C$\underline{H}_2$(CH$_2$)$_3$CH$_3$), 1.96 (—NHCOC$\underline{H}_3$), 3.22 (—N$^+$C$\underline{H}_3$), 3.5-3.7 (—O—C$\underline{H}_2$—C$\underline{H}_2$—O—), 3.4-4.1 (chitosan-$\underline{H}$-2-6), 5.51 (—C$\underline{H}$=CH$_2$), 5.86-5.99 (—CH=C$\underline{H}_2$)

Synthetic Example 14: Preparation of Dimethyldecylammonium Chitosan-g-PEGMA

Dimethyldecylammonium chitosan-g-PEGMA was prepared in the same manner as Synthetic Example 6 except for changing from trimethylammonium chitosan (0.2 g) to dimethyldecylammonium chitosan (0.2 g, see Synthetic Example 12).

$^1$H-NMR (300 MHz, D$_2$O), δ: 0.74 (—N$^+$CH$_2$CH$_2$(CH$_2$)$_7$C$\underline{H}_3$), 1.22 (—N$^+$CH$_2$CH$_2$(C$\underline{H}_2$)$_7$CH$_3$), 1.58 (—N$^+$CH$_2$ C$\underline{H}_2$(CH$_2$)$_7$CH$_3$), 1.94 (—NHCOC$\underline{H}_3$), 3.22 (—N$^+$C$\underline{H}_3$), 3.5-3.7 (—O—C$\underline{H}_2$—C$\underline{H}_2$—O—), 3.4-4.1 (chitosan-$\underline{H}$-2-6), 5.54 (—C$\underline{H}$=CH$_2$), 5.85-6.05 (—CH=C$\underline{H}_2$)

Preparation of Hydrogels

Synthetic Example 15: Photopolymerisation of Chitosan-g-PEGMA and Quaternized Chitosan-g-PEGMA Chitosan-g-PEGMA (0.06 g, see Synthetic Example 5) and PEGDA (0.06 g) were blended and dissolved in water (0.48 ml). The photoinitiator (Irgacure 2959) was added at 0.1 wt % (based on the total amount of Chitosan-g-PEGMA, PEGDA and water). The resultant solution was placed inside a mould produced from two glass plates with a 0.25 mm thick spacer frame in between. The solution was then exposed to UV light (365 nm, 15 min exposure, 10 mW/cm$^2$) using a Honle UV Technology machine equipped with a UV mercury lamp. After curing, the mould was opened, the hydrogel removed and washed with deionised water.

Similarly prepared were hydrogels produced from trimethylammonium chitosan-g-PEGMA, trihexylammonium chitosan-g-PEGMA, tridecylammonium chitosan-g-PEGMA, dimethylhexylammonium chitosan-g-PEGMA and dimethyldecylammonium chitosan-g-PEGMA.

SEM Images of Hydrogels

The SEM cross-sectional images for the freeze-dried polymers of the chitosan and some quaternized chitosan are shown in FIG. 1. FIG. 1 shows that the unquaternized chitosan hydrogel has many small pores (of a few micrometers) and the quaternized chitosan hydrogels generally have larger pores greater than 100 μm under the same magnification (×220). Dimethyldecylammonium chitosan hydrogel (Synthetic Example 14) was observed to have relatively larger pores compared to dimethylhexylammonium chitosan hydrogel (Synthetic Example 13).

APPLICATION EXAMPLES

Antimicrobial Activity

General Culture Procedure

The hydrogels prepared from photopolymerisation were soaked in phosphate saline buffer overnight and rinsed several times before antimicrobial assay. The bacterium was cultured and harvested for 24 h on Trypticase Soy Agar before it was washed twice with sterile purified water by centrifugation. The bacterial suspension (10 μl) in purified water was transferred to the centre of the hydrogel coating in the well of a tissue culture polystyrene plate. The hydrogel was in contact with the microorganism at 24° C. for 4 hours (exposure time). A small volume of neutralizing broth was then added to the well to recover any bacterial survivors. A series of 10-fold dilutions in neutralizing broth was prepared, and plated out in Trypticase Soy Agar. The plates were incubated at 35° C. for 48 hours, and counted for colony forming units. The results were expressed as:

Log reduction=Log initial count of inoculum−Log survivor count on 4 hours exposure time Results

TABLE 1

| Synthetic example No. | Log reduction | | | |
|---|---|---|---|---|
| | Pseudomonas aeruginosa | Staphylococcus aureus | Esherichia coli | Fusarium solani |
| Example 1 | 6 | 2.61 | 2.25 | 1.62 | 0.75 |
| Example 2 | 7 | 1.84 | 5.62 | 1.84 | 1.32 |
| Example 3 | 8 | 1.72 | 4.21 | 2.01 | 0.65 |
| Example 4 | 13 | 1.51 | 1.99 | 2.08 | 4.49 |
| Example 5 | 14 | 2.88 | 4.18 | 1.94 | 4.49 |
| Comparative Example | 5 | 0.26 | 0.14 | 0.08 | 0.01 |

Surface Modification of Contact Lens with Chitosan Derivative

Preparation of Monomer Solution

Figure 2:
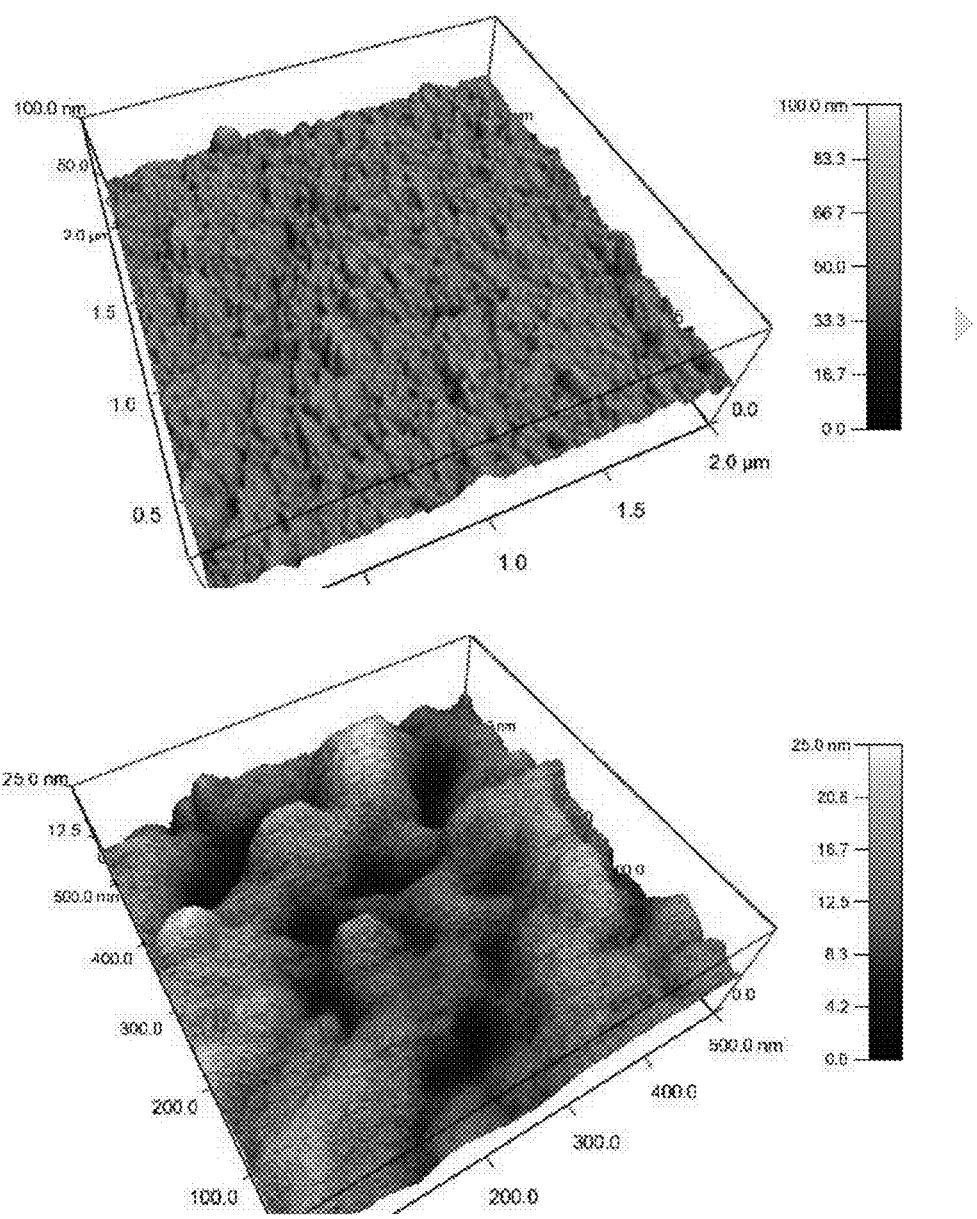
FIG. 2 shows results of Atomic Force Microscope (AFM) observation reveals that trimethylammonium chitosan-g-PEGMA hydrogel was coated on the surface of silicon-containing rigid gas permeable contact lenses (RGP CLs).
Figure 2:
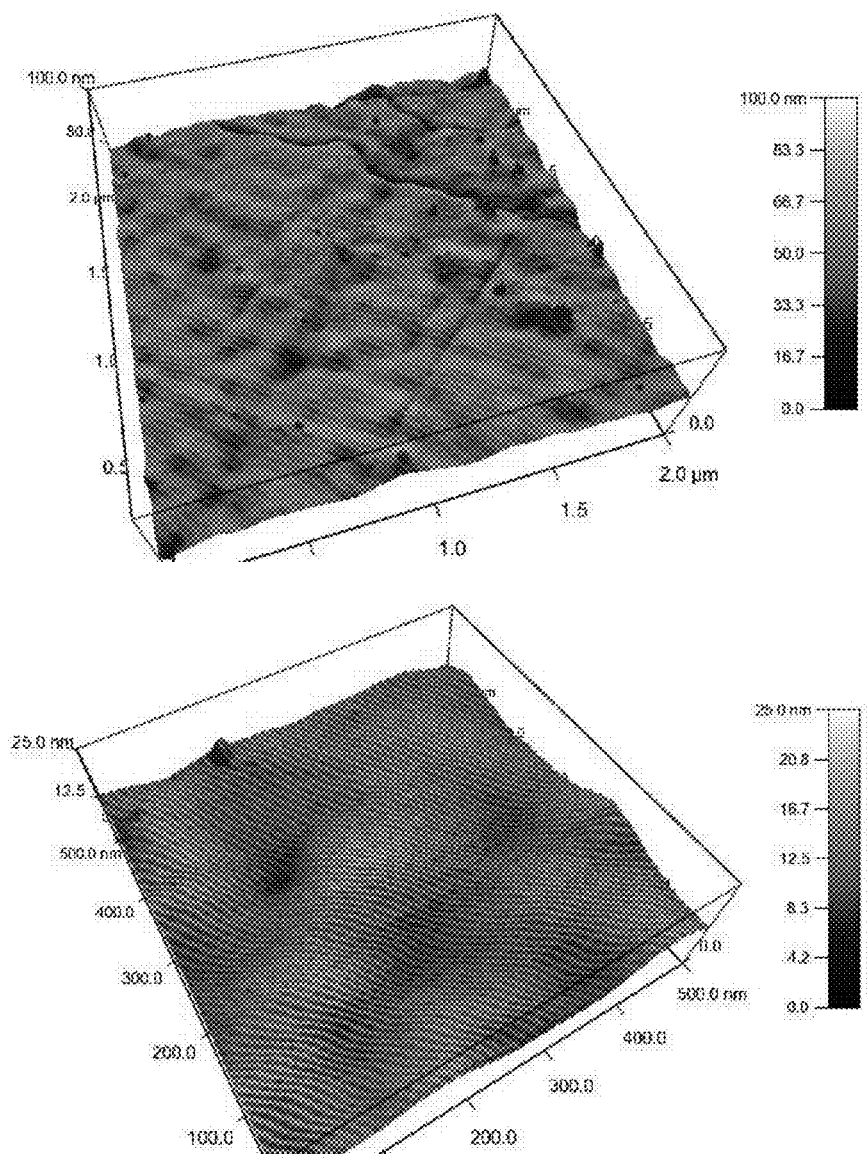
Figure 2:
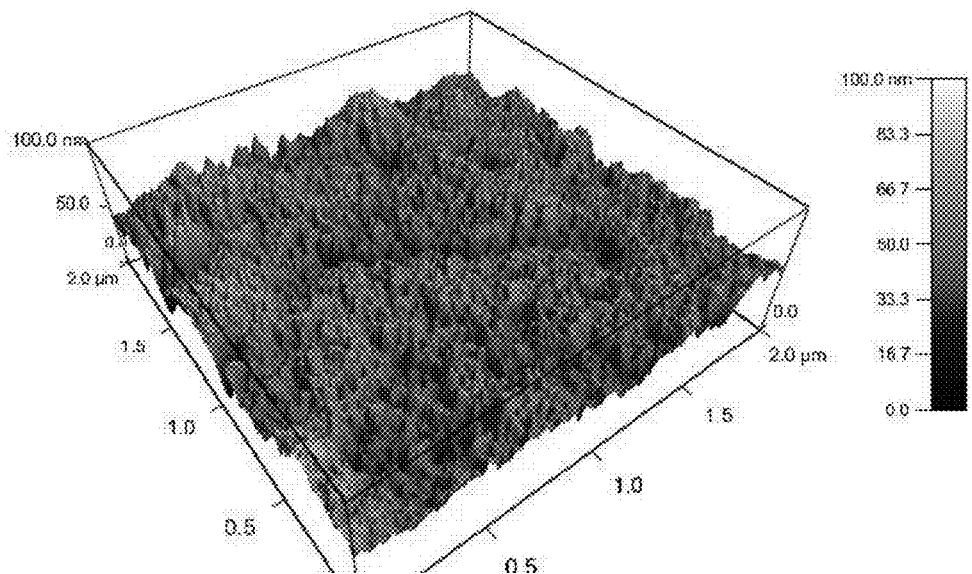
Figure 2:
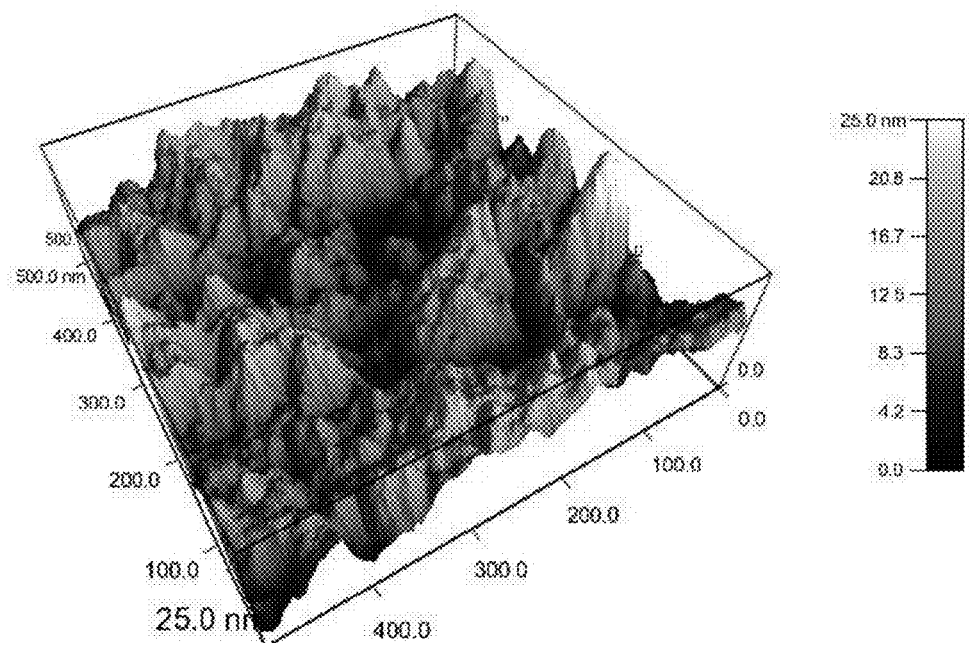

Trimethylammonium chitosan-g-PEGMA (Synthetic example 6) and PEGDA were dissolved in deionized water (monomer solution). The ratio of monomer was 2:1 and monomer concentration was 5%. Silicon-containing rigid gas permeable contact lenses (RGP CLs) were cleaned with deionized water and isopropyl alcohol for 30 minutes in PTFE beaker. And then they were dried under vacuum. The cleaned RGP CLs were treated by argon plasma for 60 seconds under a power of 50 W. Argon gas flow rate was 100 sccm. Then they were subsequently exposed to the atmosphere for 15 minutes. The plasma-treated RGP CLs and monomer solution were placed into the glove box (Argon atmosphere). They were degassed thoroughly. The RGP CLs were immersed in a small amount of monomer solution and the top of vial were screwed tightly. Then they were subjected to UV irradiation (30-35 mW/cm$^2$) for 90 minutes. Trimethylammonium chitosan-g-PEGMA coated RGP CLs (Cs-coated lens) were washed thoroughly with deionized water under ultrasonication to remove the residual monomer for more than 30 minutes. The results of AFM (Atomic Force Microscope) observation are shown in FIG. 2. FIG. 2 clearly shows that trimethylammonium chitosan-g-PEGMA was coated on the surface of the RGP CLs.

Antimicrobial Activity

Antimicrobial activity of Cs-coated lens was evaluated in the same manner as that mentioned above. The results are shown in Table 2.

TABLE 2

| | Log reduction | |
|---|---|---|
| | P. aeruginosa | E. coli |
| Cs-coated lens | 1.02 | 2.57 |

Contact Angle

The contact angle was measured by a liquid drop method at room temperature by means of contact angle meter Drop Master 500 manufactured by Kyowa Interface Science Co., Ltd.

Control (non treated): 93.4°
Cs-coated lens: 50.6°

The results reveals that the hydrogel coating of the present invention exhibits excellent antimicrobial activity and wettability.

What is claimed is:

1. A method of producing a chitosan hydrogel, comprising a step of polymerizing a polymerizable composition comprising a quaternized chitosan derivative having polymerizable organic moieties, initiator, and water,
   wherein said polymerizing comprises a step of irradiating ultraviolet (UV) to a photopolymerizable composition comprising a quaternized chitosan derivative having polymerizable organic moieties, photoinitiator, and water,
   wherein said quaternized chitosan derivative has the following formula,

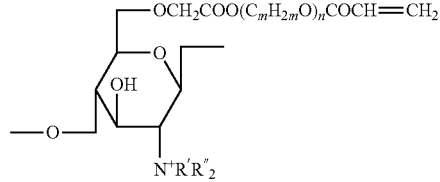

wherein R' and R" are independently selected from the group consisting of optionally substituted $C_1$-$C_{18}$ alkyl, m is 2 or 3, n is 1 to 20.

2. The method of claim 1, wherein R' has more carbon atoms than R".

3. The method of claim 1, wherein said quaternized chitosan derivative is produced by a method comprising a step of reacting a quaternized chitosan derivative and a halide represented by the following formula:

wherein X is a halogen atom.

* * * * *